United States Patent
Lee et al.

(10) Patent No.: US 9,298,194 B2
(45) Date of Patent: Mar. 29, 2016

(54) METHOD TO CONTROL MEDICAL EQUIPMENT

(75) Inventors: Kwang Kyu Lee, Yongin-si (KR); San Lim, Suwon-si (KR); Kyung Won Moon, Seongnam-si (KR); Kyung Shik Roh, Seongnam-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 593 days.

(21) Appl. No.: 13/317,999

(22) Filed: Nov. 2, 2011

(65) Prior Publication Data
US 2012/0136480 A1      May 31, 2012

(30) Foreign Application Priority Data
Nov. 30, 2010   (KR) .................. 10-2010-0120310

(51) Int. Cl.
G05B 19/04        (2006.01)
A61B 6/10         (2006.01)
G05D 15/01        (2006.01)
A61B 6/00         (2006.01)

(52) U.S. Cl.
CPC .............. G05D 15/01 (2013.01); A61B 6/102 (2013.01); A61B 6/107 (2013.01); A61B 6/4441 (2013.01); A61B 6/4447 (2013.01); A61B 6/4452 (2013.01)

(58) Field of Classification Search
CPC .. A61B 6/4441; A61B 6/4476; A61B 6/4482; A61B 6/102; A61B 6/107; G05B 2219/36429
USPC .......... 700/245, 255, 257, 260, 264; 378/195, 378/196, 197
See application file for complete search history.

(56) References Cited

U.S. PATENT DOCUMENTS

| | | | | |
|---|---|---|---|---|
| 4,208,586 A * | 6/1980 | Craig et al. | .................... | 378/189 |
| 6,233,504 B1 * | 5/2001 | Das et al. | ...................... | 700/260 |
| 6,385,509 B2 * | 5/2002 | Das et al. | ...................... | 700/260 |
| 6,430,473 B1 * | 8/2002 | Lee et al. | ...................... | 700/245 |

(Continued)

FOREIGN PATENT DOCUMENTS

WO     WO 2010128417 A1 *  11/2010

OTHER PUBLICATIONS

A. Aristidou and J. Lasenby, "Inverse Kinematics: a review of existing techniques and introduction of a new fast iterative solver," University of Cambridge, 2009.*

(Continued)

Primary Examiner — Thomas G Black
Assistant Examiner — Peter D Nolan
(74) Attorney, Agent, or Firm — Harness, Dickey & Pierce, P.L.C.

(57) ABSTRACT

A method to control medical equipment that moves along at least one axis or performs joint movement is provided. While the medical equipment is passively moved as operated by the operator, the operation intention of the operator is determined using a force sensor, a torque sensor, or the like, and motor control is performed taking into consideration the determined operation intention to reduce load (or drive power) of the operator. To accomplish this, the method determines a direction and magnitude of force that an operator applies to the medical equipment to move the medical equipment and generates auxiliary force having a magnitude proportional to the force applied by the operator and having the same direction as the direction of the force applied by the operator such that the medical equipment may be moved.

12 Claims, 6 Drawing Sheets

(56) References Cited

U.S. PATENT DOCUMENTS

| | | | |
|---|---|---|---|
| 7,029,175 B2* | 4/2006 | Karaus et al. | 378/197 |
| 7,093,976 B2* | 8/2006 | Fadler et al. | 378/197 |
| 7,160,027 B2* | 1/2007 | Bauer et al. | 378/197 |
| 7,175,346 B2* | 2/2007 | Heinze et al. | 378/197 |
| 7,302,040 B2* | 11/2007 | Camus | 378/117 |
| 7,428,296 B2* | 9/2008 | Bernhardt et al. | 378/117 |
| 7,519,441 B2* | 4/2009 | Boomgaarden | 700/63 |
| 7,564,949 B2* | 7/2009 | Sattler et al. | 378/117 |
| 7,953,509 B2* | 5/2011 | Murayama | 700/114 |
| 8,024,071 B2* | 9/2011 | Komatsu et al. | 700/258 |
| 8,529,128 B2* | 9/2013 | Horiuchi | 378/197 |
| 2002/0088055 A1* | 7/2002 | Vogel et al. | 5/600 |
| 2006/0274888 A1* | 12/2006 | Bernhardt et al. | 378/117 |
| 2007/0086570 A1* | 4/2007 | Spahn | 378/117 |
| 2008/0098525 A1* | 5/2008 | Doleschal et al. | 5/600 |
| 2009/0022275 A1* | 1/2009 | Grebner et al. | 378/95 |
| 2009/0212478 A1* | 8/2009 | Murayama | 269/56 |
| 2009/0259412 A1* | 10/2009 | Brogardh | 702/41 |
| 2010/0137882 A1 | 6/2010 | Quaid, III | |

OTHER PUBLICATIONS ("PID controller", Wikipedia.org, Dec. 2008 [https://web.archive.org/web/20081205094951/http://en.wikipedia.org/wiki/PID_controller].*

* cited by examiner

FIG. 1(A)
FIG. 1(B)
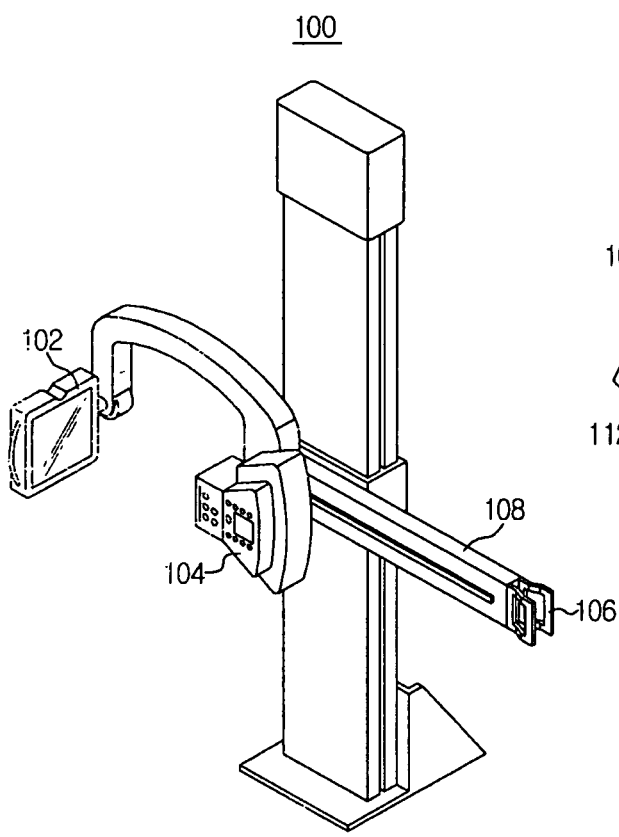
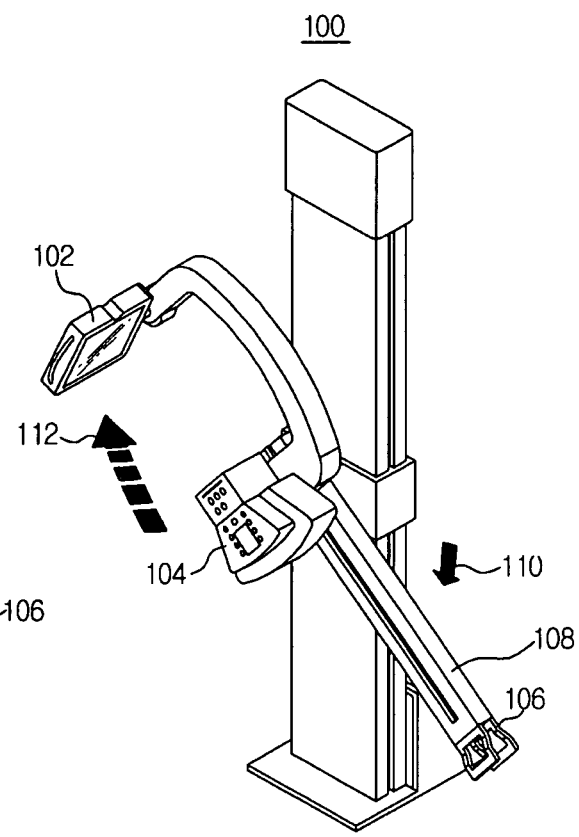

METHOD TO CONTROL MEDICAL EQUIPMENT

CROSS-REFERENCE TO RELATED APPLICATIONS

This application claims the priority benefit of Korean Patent Application No. 10-2010-0120310, filed on Nov. 30, 2010 in the Korean Intellectual Property Office, the disclosure of which is incorporated herein by reference.

BACKGROUND

1. Field

Embodiments relate to a method to control medical equipment that is large and heavy.

2. Description of the Related Art

Positioning modes of large and heavy medical equipment are mainly classified into an automatic motorized positioning mode in which motor drive power is used to position the medical equipment to a position input by an operator and a manual positioning mode in which the operator manually positions the medical equipment to a desired position using a handle without using motor drive power.

In the automatic motorized positioning mode, it takes a long time to complete positioning since drive speed is limited in order to secure stability or the like. Thus, most hospitals prefer manual positioning to automatic motorized positioning to improve profitability. However, although manual positioning has a short positioning time compared to automatic motorized positioning, repeated tasks for manual positioning impose heavy burden on the operator since the operator manually moves the heavy equipment.

SUMMARY

Therefore, it is an aspect of one or more embodiments to provide a method to control medical equipment wherein, while the medical equipment is passively moved as operated by the operator, the operation intention of the operator is determined using a force sensor, a torque sensor, or the like and motor control is performed taking into consideration the determined operation intention to reduce load (or drive power) of the operator.

It is another aspect of one or more embodiments to provide a method to control medical equipment wherein virtual force similar to magnetic attractive force is applied with respect to frequently used positions of the medical equipment to allow the operator to easily position the equipment to a desired one of the frequently used positions.

It is a further aspect of one or more embodiments to provide a method to control medical equipment wherein virtual force similar to magnetic attractive force is used to allow the operator to easily align different structures or the like.

Additional aspects of one or more embodiments will be set forth in part in the description which follows and, in part, will be apparent from the description, or may be learned by practice of the invention.

In accordance with one aspect of one or more embodiments, a method to control medical equipment that moves along at least one axis or performs joint movement includes determining a direction and magnitude of force that an operator applies to the medical equipment to move the medical equipment, and generating auxiliary force having a magnitude proportional to the force applied by the operator and having the same direction as the direction of the force applied by the operator such that the medical equipment is easily moved.

In the method, an impedance filter receives information of the force applied by the operator from a force sensor and generates information of a new position of the medical equipment, and a position controller receives the information of the new position of the medical equipment from the impedance filter and receives position information fed back from the motor and generates position control information of the medical equipment.

In the method, the force sensor is a strain gauge.

In the method, the position controller receives position information fed back from at least one of an encoder and a potentiometer of the motor.

In accordance with another aspect of one or more embodiments, a method to control medical equipment that moves along at least one axis or performs joint movement includes determining a direction and magnitude of force that an operator applies to the medical equipment to move the medical equipment, and generating first auxiliary force having a magnitude proportional to the force applied by the operator and having the same direction as the direction of the force applied by the operator such that the medical equipment is easily moved in the direction of the force applied by the operator and generating, when the medical equipment has approached a preset position, a second auxiliary force having a direction opposite to the direction of the force applied by the operator to stop the medical equipment at the preset position such that the medical equipment is correctly positioned to the preset position.

In the method, an impedance filter receives information of the force applied by the operator from a force sensor and generates information of a new position of the medical equipment, and a position controller receives the information of the new position of the medical equipment from the impedance filter and receives position information fed back from the motor and generates position control information of the medical equipment.

BRIEF DESCRIPTION OF THE DRAWINGS

These and/or other aspects of the invention will become apparent and more readily appreciated from the following description of the embodiments, taken in conjunction with the accompanying drawings of which:

FIGS. 1(A) and 1(B) illustrate a control concept of medical equipment according to an embodiment;

DETAILED DESCRIPTION

Figure 2:
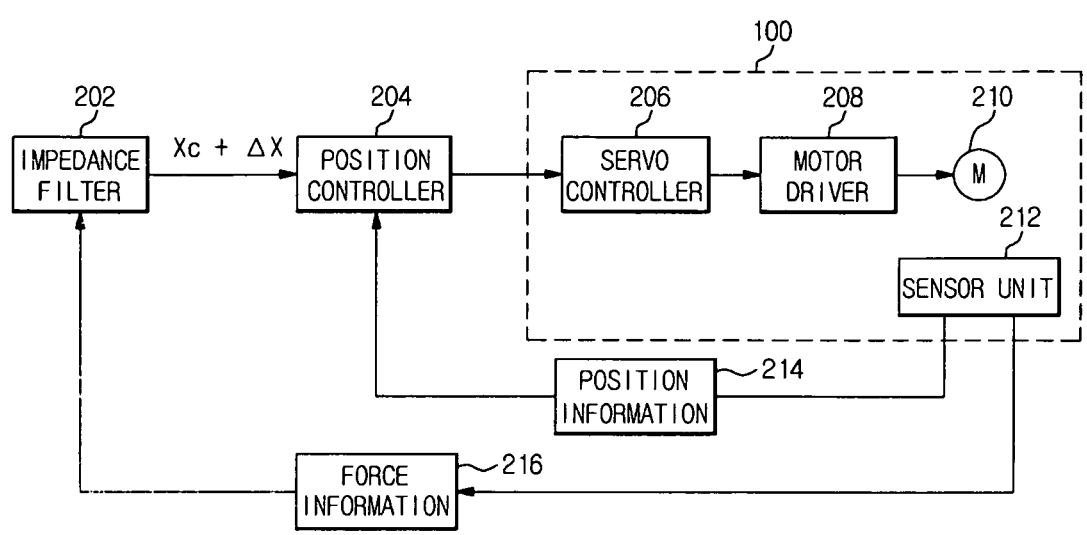
FIG. 2 illustrates control flow of the medical equipment shown in FIGS. 1(A) and 1(B)

Reference will now be made in detail to the embodiments, examples of which are illustrated in the accompanying drawings, wherein like reference numerals refer to like elements throughout.

FIGS. 1(A) and 1(B) illustrate a control concept of medical equipment according to an embodiment. The medical equipment shown in FIGS. 1(A) and 1(B) is an X-ray imaging apparatus 100 that includes an imaging unit 102, a user interface 104, and a handle 106. The imaging unit 102 includes an image surface on which imaging is actually performed. The user interface 104 allows an operator of the X-ray imaging apparatus 100 to perform operation (or manipulation), setting, and the like that may be required for X-ray imaging. The operator of the X-ray imaging apparatus 100 may move an arm 108 using the handle 106 to adjust the position of the imaging unit 102. Although not illustrated, when the imaging unit 102 has reached a target position, a fixing device (not shown) is used to fix the arm 108 such that the arm 108 does not move.

As shown in FIG. 1(B), if the operator moves the handle 106 in a direction and with a magnitude of force as indicated by arrow 110 in order to position the imaging unit 102 to a higher position than in FIG. 1(A), the imaging unit 102 moves upward in a direction and with a magnitude of force as indicated by arrow 112. Here, since the magnitude of force 110 applied to the handle 106 is smaller than the magnitude of force 112 applied to move the imaging unit 102, the operator may easily move the heavy imaging unit 102 to a desired position with small force 110. This may be implemented by increasing drive power of a motor provided on each axis of the medical equipment taking into consideration the direction and magnitude of force applied to the handle 106 such that force greater than the force applied to the handle 106 is created in the same direction as the direction of the force applied to the handle 106. The auxiliary force having a magnitude proportional to the force applied by the operator and having the same direction as the direction of the force applied by the operator, may be generated to move the medical equipment easily.

FIG. 2 illustrates control flow of the medical equipment shown in FIGS. 1(A) and 1(B). In FIG. 2, a dashed block denoted by reference numeral 100 indicates the medical equipment 100 of FIGS. 1(A) and 1(B). A servo controller 206, a motor driver 208, a motor 210, and a sensor unit 212 shown inside the dashed block (i.e., the medical equipment) 100 are partial hardware components of the medical equipment 100 and an impedance filter 202, a position controller 204, position information 214, and force information 216 shown outside the dashed block 100 illustrate processes or modules associated with calculation performed by a microcomputer (i.e., a main controller) of the medical equipment 100 and flow of information transmitted to the microcomputer.

Control of the medical equipment 100 according to an embodiment is based on admittance control, and position control of the medical equipment 100 is performed in combination with indirect force control.

To accomplish this, first, the operator measures the direction and magnitude of force applied to the handle 106 of the medical equipment 100 using a force sensor of the sensor unit 212. A response of the control system of the medical equipment 100 to the force F applied by the operator is determined using an impedance filter represented by the following Equation 1.

$$F = M_d \Delta \ddot{x} + B_d \Delta \dot{x} \qquad \text{Equation 1}$$

In Equation 1, F denotes force applied by the operator, measured through the force sensor, and $M_d$ and $B_d$ denote the weight and friction of the medical equipment 100 that are actually felt by the operator. The weight $M_d$ and the friction $B_d$ may vary and may be adjusted and set within a predetermined stabilized range according to operator convenience. Although a spring force term is added to Equation 1 in the case of a general impedance filter, spring stiffness is set to 0 in the embodiment since the desired position of the medical equipment 100 is constantly changed due to the force F applied by the operator. "Δx" in Equation 1 is a change of the current position due to the force F applied by the operator. Accordingly, a new target position of each time is $x_c + \Delta x$ when an immediately previous target position is $x_c$.

In addition, since the change of the current position (Δx), the second derivative of Δx ($\Delta \ddot{x}$), and the first derivative of Δx ($\Delta \dot{x}$) are proportional to the force F applied by the operator, the positioning speed of the medical equipment 100 (i.e., the speed at which the medical equipment 100 reaches a target position) may increase in proportion to the force F. When the operator no longer applies force (i.e., F=0), the medical equipment 100 does not move any further since Δx converges to 0 in Equation 1. Here, the highest acceleration and highest speed of movement of the medical equipment 100 may be limited by setting the highest values of $\Delta \ddot{x}$ and $\Delta \dot{x}$ taking into consideration safety of the medical equipment 100 and the imaging subject such as a patient, a sample, or the like.

The position controller 204 performs position control based on current position information 214 of the motor 210, which has been fed back to the position controller 204, using position information $x_c + \Delta x$ corrected by the impedance filter 202 as a control command.

Specifically, as shown in FIG. 2, when the impedance filter 202 generates corrected position information $x_c + \Delta x$, the position controller 204 of the medical equipment 100 generates a control command to perform servo control based on the position information and the servo controller 206 drives the motor 210 through the motor driver 208 based on the control command. The position controller 204 receives, as feedback information, position information 214 of each part of the medical equipment 100 obtained through a position sensor such as an encoder or a potentiometer of the motor 210 and generates a position control command taking into consideration the position information 214. The impedance filter 202 also receives, as feedback information, force information 216 (for example, information of the force 110 of FIGS. 1(A) and 1(B)) of force applied to the medical equipment 100 measured through a force sensor of the sensor unit 212 and generates position information taking into consideration the force information 216.

Figure 3:
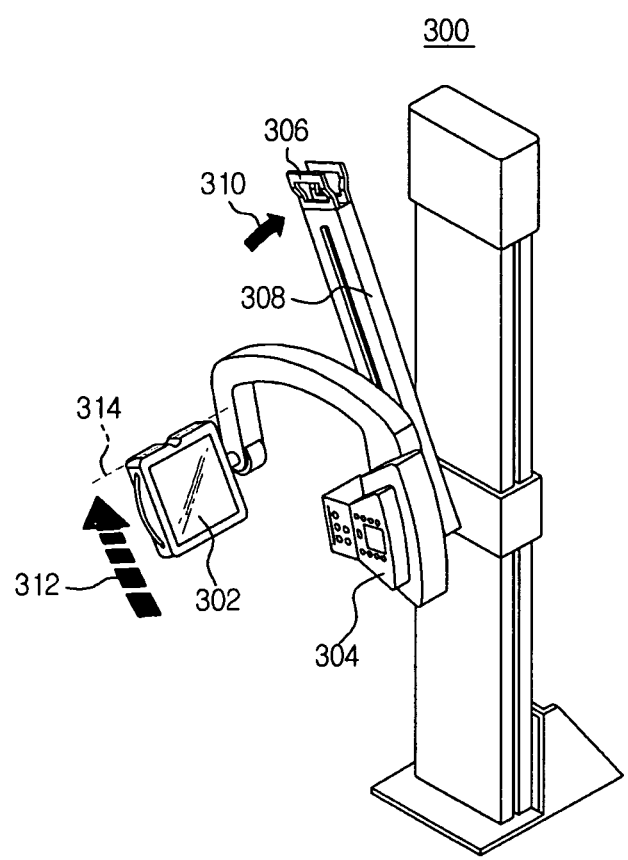
FIG. 3 illustrates a control concept of medical equipment according to another embodiment.

FIG. 3 illustrates a control concept of medical equipment according to another embodiment. The medical equipment shown in FIG. 3 is an X-ray imaging apparatus 300 that includes an imaging unit 302, a user interface 304, and a handle 306. The imaging unit 302 includes an image surface on which imaging is actually performed. The user interface 304 allows an operator of the X-ray imaging apparatus 300 to perform operation (or manipulation), setting, and the like that may be required for X-ray imaging. The operator of the X-ray imaging apparatus 300 may move an arm 308 using the handle 306 to adjust the position of the imaging unit 302. When the imaging unit 302 has reached a preset position, movement of the X-ray imaging apparatus 300 stops.

As shown in FIG. 3, if the operator moves the handle 306 in a direction and with a magnitude of force as indicated by arrow 310 in order to change the position of the imaging unit 302, the imaging unit 302 moves upward in a direction and with a magnitude of force as indicated by arrow 312. Here, since the magnitude of force 310 applied to the handle 306 is smaller than the magnitude of force 312 applied to move the imaging unit 302, the operator may easily move the heavy imaging unit 302 to a desired position with small force 310. This may be implemented by increasing drive power of a motor provided on each axis of the medical equipment taking into consideration the direction and magnitude of force applied to the handle 306 such that force greater than the force applied to the handle 306 is created in the same direction as the direction of the force applied to the handle 306. The auxiliary force having a magnitude proportional to the force applied by the operator and having the same direction as the direction of the force applied by the operator, may be generated to move the medical equipment easily. Reference numeral 314 indicates a preset target position of the imaging unit 302. When the imaging unit 302 has approached the target position 314 by drive power of the motor, the speed of the imaging unit 302 (or force applied to the imaging unit 302) is gradually reduced and movement of the imaging unit 302 stops upon reaching the target position 314. A guide function to position the imaging unit 302 to a preset target position, which is referred to as "snap to grid", is implemented in this manner. Using this guide function, the operator may easily move the imaging unit 302 with small force and may also correctly position the imaging unit 302 to the target position 314 since movement of the imaging unit 302 stops at the target position 314.

Figure 4:
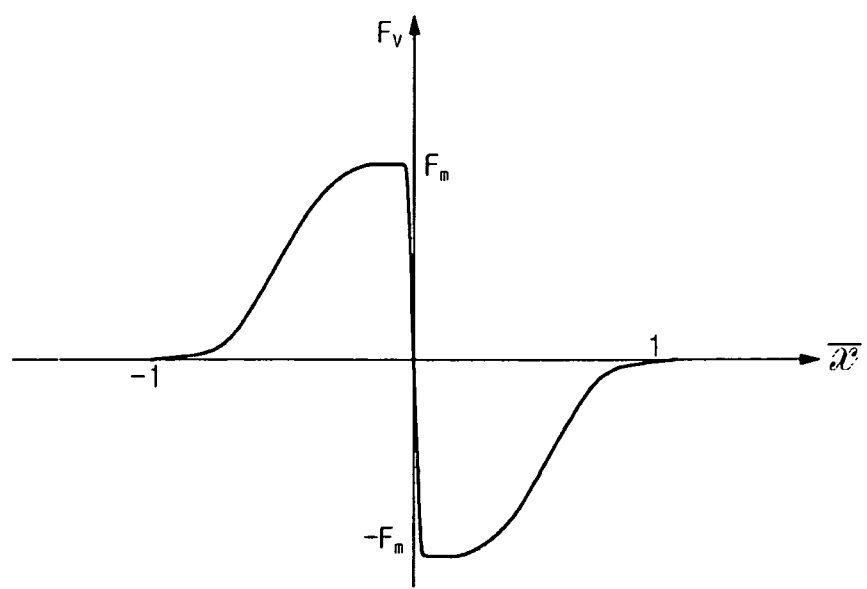
FIG. 4 is a graph illustrating control concept of the medical equipment shown in FIG. 3.

FIG. 4 is a graph illustrating a control concept of the medical equipment shown in FIG. 3. In the control method of FIG. 3, frequently used positions are preset as target positions and positions of each motion axis corresponding to the target positions are set at specific intervals and virtual force is generated with respect to each of the set positions such that, when the medical equipment approaches each target position, the generated virtual force causes the medical equipment to stop upon reaching the target position.

When a frequently used position, a target position that may need to be reported to the operator, or the like is represented by x*, virtual attractive force $F_v$ generated with respect to the target position x* is represented by the following Equation 2.

$$F_v = \begin{cases} 0 & \text{for } \|x^* - x\| > x_v \\ f(\bar{x}, F_m) & \text{otherwise} \end{cases} \quad \text{Equation 2}$$

In Equation 2, $X_v$ represents a range in which virtual attractive force $F_v$ is applied with respect to the target position x*. As shown in Equation 2, the virtual attractive force $F_v$ is 0 when the current position is more distant from the target position x* than $x_v$, otherwise the virtual attractive force $F_v$ is determined to be a function of $\bar{x}$ and $F_m$. The virtual attractive force $F_v$ is graphically represented in FIG. 4.

In Equation 2, $$\bar{x} = \frac{x^* - x}{x_v}$$

and $F_m$ is the maximum of the virtual attractive force $F_v$.

The guide function (i.e., snap to grid) to position the imaging unit 302 to a desired position is implemented by adding the virtual attractive force $F_v$ calculated from Equation 2 to the force F of Equation 1 and performing control of embodiment of FIGS. 1(A) and 1(B) or FIG. 3 according to the resulting force $F_v$+F. Here, it is to be noted that $F_m$ is set such that the medical equipment may escape from the target position x* since the medical equipment may not be able to escape from the target position x* if $F_m$ is too great.

Figure 5:
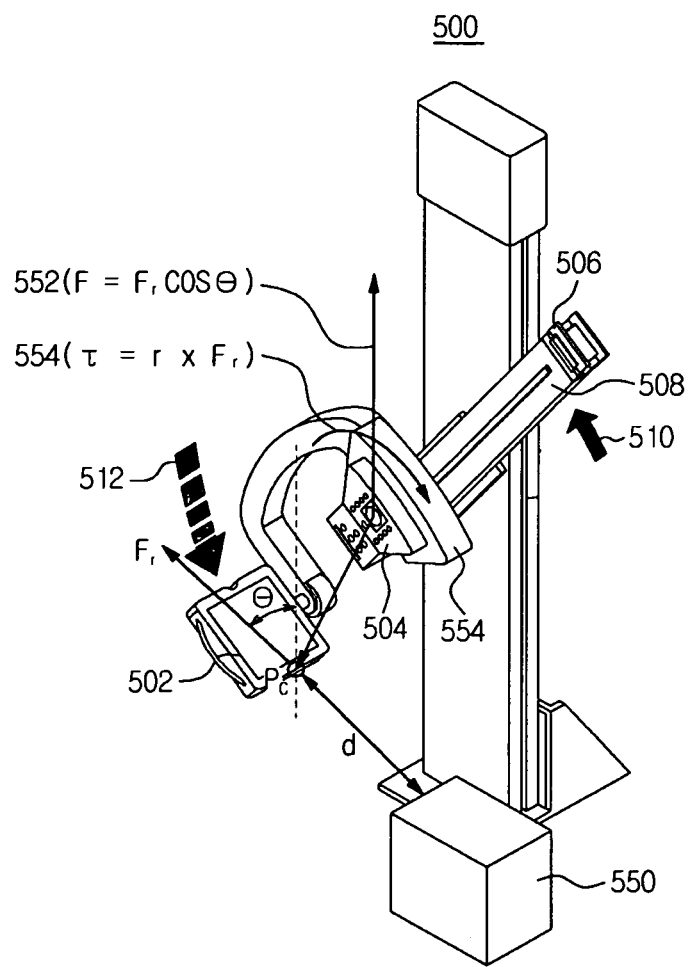
FIG. 5 illustrates a control concept of medical equipment according to another embodiment.

FIG. 5 illustrates a control concept of medical equipment according to another embodiment. The medical equipment shown in FIG. 5 is an X-ray imaging apparatus 500 that includes an imaging unit 502, a user interface 504, and a handle 506. The imaging unit 502 includes an image surface on which imaging is actually performed. The user interface 504 allows an operator of the X-ray imaging apparatus 500 to perform operation (or manipulation), setting, and the like that may be required for X-ray imaging. The operator of the X-ray imaging apparatus 500 may move an arm 508 using the handle 506 to adjust the position of the imaging unit 502.

As shown in FIG. 5, if the operator moves the handle 506 in a direction and with a magnitude of force as indicated by arrow 510 in order to change the position of the imaging unit 502, the imaging unit 502 moves downward in a direction and with a magnitude of force as indicated by arrow 512. Here, since the magnitude of force 510 applied to the handle 506 is smaller than the magnitude of force 512 applied to move the imaging unit 502, the operator may easily move the heavy imaging unit 502 to a desired position with small force 510. This may be implemented by increasing drive power of a motor provided on each axis of the medical equipment taking into consideration the direction and magnitude of force applied to the handle 506 such that force greater than the force applied to the handle 506 is created in the same direction as the direction of the force applied to the handle 506. The auxiliary force having a magnitude proportional to the force applied by the operator and having the same direction as the direction of the force applied by the operator, may be generated to move the medical equipment easily.

However, when the imaging unit 502 approaches another structure 550 while moving in a direction toward an arrow 512, the speed of the imaging unit 502 is reduced to zero such that the imaging unit 502 does not collide with the structure 550. Collision avoidance and joint limit avoidance during operation of the X-ray imaging apparatus 500 are implemented by calculating the distance between each joint of the X-ray imaging apparatus 500, the distance between each joint of the X-ray imaging apparatus 500 and each structure 550 located around the X-ray imaging apparatus 500, or the distance between each structure 550 located around the X-ray imaging apparatus 500 using position information of each joint (or part) of the X-ray imaging apparatus 500 and position information of each structure 550. In FIG. 5, F (552) and T (554) denote virtual forces applied to the medical equipment 500 in order to avoid collision.

Figure 6:
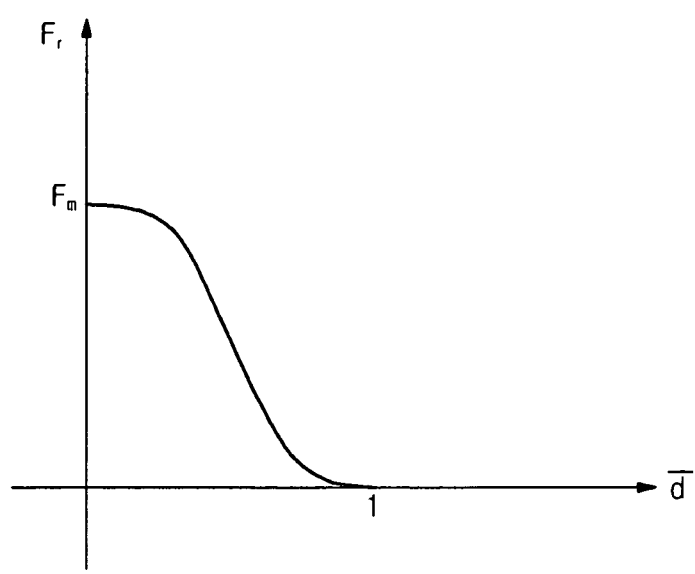
FIG. 6 is a graph illustrating a control concept of the medical equipment shown in FIG. 5.

FIG. 6 is a graph illustrating a control concept of the medical equipment shown in FIG. 5. In the control method of FIG. 5, when the distance d between the current joint position and each joint limit or the shortest distance between the X-ray imaging apparatus 500, and each structure is shorter than a specific safe distance $d_m$, virtual repulsive force $F_r$ is calculated and added to the force F of Equation 1 and control of the embodiment of FIGS. 1(A) and 1(B) is performed according to the resulting force to avoid each joint limit or avoid collision with another structure 550.

In addition, not only collision of the X-ray imaging apparatus 500 with a structure 550 located around the X-ray imaging apparatus 500 may be avoided, but also collision with an external obstacle may be avoided by measuring the distance between the medical equipment 500 and the structure 550 and the distance between the medical equipment 500 and the external obstacle using an additional sensor such as a distance sensor which may be included in the sensor unit 212.

The magnitude of virtual repulsive force $F_r$ may be defined based on distance information as shown in Equation 3 and the direction of the virtual repulsive force $F_r$ may be defined to be a direction toward which the shortest distance between structures that may collide increases.

$$F_v = \begin{cases} 0 & \text{for } \|\overline{d}\| > 1 \\ f(\overline{d}, F_m) & \text{otherwise} \end{cases} \quad \text{Equation 3}$$

In FIG. 5, the directions of forces indicated by 552 and 554 are the motion axis directions of joints to avoid collision. When $P_c$ represents a point on a structure at which collision may occur and q represents a set of variables indicating motions of the joints, the virtual repulsive forces $F_r$ of drivers of the joints may be represented by the following Equation 4.

$$\tau = \left(\frac{\partial P_C}{\partial q}\right)^T F_r = J_C^T F_r \quad \text{Equation 4}$$

In Equation 4, $J_c$ represents Jacobian corresponding to the collision point $P_c$.

As is apparent from the above description, according to embodiments, it may be possible for the operator to easily and intuitively position heavy equipment since the intention of the operator is determined and motors of the equipment are controlled taking into consideration the intention of the operator.

In addition, it may be possible to reduce operator load while increasing positioning speed compared to conventional automatic motorized positioning.

Further, through the (snap to grid) function to guide equipment to a frequently used position, it may be possible to improve user convenience while increasing positioning accuracy.

Furthermore, it may be possible to allow the operator to avoid collision, joint limit, or the like by haptically informing the operator of the risk of collision, joint limit, or the like.

Although the method to control medical equipment is described with an X-ray imaging apparatus shown in FIGS. 1-6 as one or more embodiments, the method to control medical equipment is not limited to an X-ray imaging apparatus.

Although a few embodiments have been shown and described, it would be appreciated by those skilled in the art that changes may be made in embodiments without departing from the principles and spirit of the invention, the scope of which is defined in the claims and their equivalents.

What is claimed is:

1. A method to control medical equipment that moves along at least one axis or performs joint movement, the method comprising:
   determining a direction and magnitude of force that an operator applies to the medical equipment to move the medical equipment;
   generating auxiliary force having a magnitude proportional to the force applied by the operator and having a same direction as the direction of the force applied by the operator; and
   calculating virtual repulsive force to avoid each joint limit of the medical equipment and collision with another obstacle by calculating a distance between each joint of the medical equipment and by measuring a distance between the medical equipment and the obstacle using a distance sensor;
   wherein a direction of the virtual repulsive force is defined to be a direction to avoid each joint limit of the medical equipment and to avoid collision with the obstacle, and wherein the auxiliary force is generated such that a speed and an acceleration of the medical equipment is less than a predetermined maximum speed and a predetermined maximum acceleration, respectively, of the medical equipment.

2. The method according to claim 1, wherein an impedance filter is configured to receive information of the force applied by the operator from a force sensor, and is configured to generate information of a new position of the medical equipment, and
   wherein a position controller is configured to receive the information of the new position of the medical equipment from the impedance filter, is configured to receive position information fed back from the motor, and is configured to generate position control information of the medical equipment.

3. The method according to claim 2, wherein the force sensor is configured to determine an intention of the operator.

4. The method according to claim 2, wherein the position controller is configured to receive position information fed back from at least one of an encoder and a potentiometer of the motor.

5. The method according to claim 2, wherein the force sensor is at least one of a strain gauge and a pressure sensor.

6. The method according to claim 1, further comprising:
   generating a virtual attractive force configured to cause the medical equipment to stop upon reaching a preset position.

7. The method according to claim 1, wherein the virtual repulsive force is determined with respect to a Jacobian of a collision point between the medical equipment and the obstacle.

8. A method to control medical equipment that moves along at least one axis or performs joint movement, the method comprising:
   determining a direction and magnitude of force that an operator applies to the medical equipment to move the medical equipment; and
   generating first auxiliary force having a magnitude proportional to the force applied by the operator and having a same direction as the direction of the force applied by the operator, and generating, when the medical equipment has approached a preset position, second auxiliary force in a direction toward the preset position such that the medical equipment is positioned to the preset position;
   wherein the second auxiliary force is determined depending on a distance between the preset position and the medical equipment,
   wherein the first auxiliary force is generated such that a speed and an acceleration of the medical equipment is less than a predetermined maximum speed and a predetermined maximum acceleration, respectively, of the medical equipment, and
   wherein a magnitude of the second auxiliary force is determined according to a preset maximum second auxiliary force value and a value $\overline{x}$ determined according to the equation:

$$\overline{x} = \frac{x^* - x}{x_v}$$

where x is a current position of the medical equipment, where $x^*$ is the preset position, and where $x_v$ represents a range that extends on both sides of the preset position in which the second auxiliary force is applied with respect to the preset position, wherein an impedance filter is configured to receive information of the force applied by the operator from a force sensor, and is configured to generate information of a new position of the medical equipment, and wherein a position controller is configured to receive the information of the new position of the medical equipment from the impedance filter, is configured to receive position information fed back from the motor, and is configured to generate position control information of the medical equipment.

9. The method according to claim 8, wherein the force sensor is at least one of a strain gauge and a pressure sensor.

10. The method according to claim 8, wherein the position controller is further configured to receive position information fed back from at least one of an encoder and a potentiometer of the motor.

11. The method according to claim 8, wherein the force sensor is configured to determine an intention of the operator.

12. A method to control medical equipment that moves along at least one axis or performs joint movement, the method comprising:

determining a direction and magnitude of force that an operator applies to the medical equipment to move the medical equipment; and generating first auxiliary force having a magnitude proportional to the force applied by the operator and having a same direction as the direction of the force applied by the operator, and generating, when the medical equipment has approached a preset position, second auxiliary force in a direction toward the preset position such that the medical equipment is positioned to the preset position; and calculating virtual repulsive force to avoid collision with another obstacle by measuring the distance between the medical equipment and the obstacle using a distance sensor, wherein the second auxiliary force is determined depending on a distance between the preset position and the medical equipment, wherein the first auxiliary force is generated such that a speed and an acceleration of the medical equipment is less than a predetermined maximum speed and a predetermined maximum acceleration, respectively, of the medical equipment, and wherein a magnitude of the second auxiliary force is determined according to a preset maximum second auxiliary force value and a value $\bar{x}$ determined according to the equation:

$$\bar{x} = \frac{x^* - x}{x_v}$$

where x is a current position of the medical equipment, where x* is the preset position, and where $x_v$ represents a range that extends on both sides of the preset position in which the second auxiliary force is applied with respect to the preset position.

* * * * *